(12) United States Patent
Tolton et al.

(10) Patent No.: US 8,198,589 B2
(45) Date of Patent: Jun. 12, 2012

(54) REMOTE SENSING OF GAS LEAKS

(75) Inventors: Boyd T. Tolton, Edmonton (CA);
Adrian Banica, Edmonton (CA);
Douglas W. Miller, Saskatoon (CA)

(73) Assignee: Synodon Inc., Edmonton (CA)

( * ) Notice: Subject to any disclaimer, the term of this patent is extended or adjusted under 35 U.S.C. 154(b) by 0 days.

(21) Appl. No.: 12/939,995

(22) Filed: Nov. 4, 2010

(65) Prior Publication Data

US 2011/0133089 A1  Jun. 9, 2011

Related U.S. Application Data

(63) Continuation of application No. 10/799,444, filed on Mar. 12, 2004, now Pat. No. 7,855,367.

(60) Provisional application No. 60/455,225, filed on Mar. 13, 2003.

(30) Foreign Application Priority Data

Feb. 16, 2004 (CA) .................................. 2458123

(51) Int. Cl.
*G01N 21/85* (2006.01)
(52) U.S. Cl. .................................................. 250/338.5
(58) Field of Classification Search ............... 250/338.5
See application file for complete search history.

(56) References Cited

U.S. PATENT DOCUMENTS 4,996,427 A * 2/1991 Noble et al. .................. 250/332
2003/0219094 A1* 11/2003 Basting et al. ................. 378/34

* cited by examiner

*Primary Examiner* — David Porta
*Assistant Examiner* — Djura Malevic
(74) *Attorney, Agent, or Firm* — Christensen O'Connor Johnson Kindness PLLC

(57) ABSTRACT

A gas filter correlation radiometer mounted on an aircraft is flown over a target area. The gas filter correlation radiometer is configured to detect ethane ($C_2H_6$) gas in the event of a gas leak. The gas filter correlation radiometer uses background radiation to detect ethane.

10 Claims, 5 Drawing Sheets

REMOTE SENSING OF GAS LEAKS

CROSS-REFERENCE TO OTHER APPLICATIONS

This application claims priority from U.S. provisional application 60/455,225 filed Mar. 13, 2003.

BACKGROUND OF THE INVENTION

This invention relates to remote sensing techniques to detect gas leaks. In particular, the invention involves flying an aircraft with a remote sensing instrument over a target area, such as a pipeline, and measuring absorption of upwelling electromagnetic radiation that has passed through natural gas.

Past attempts to remotely detect natural gas leaks have involved detecting increased concentrations of methane ($CH_4$). $CH_4$ comprises approximately 95% of the composition of natural gas, which makes it a natural target for detection. One problem that has been experienced is that $CH_4$ exists in fairly large quantities in the atmosphere (it is well mixed in the atmosphere with a concentration of approximately 1.7 ppm). Therefore, detecting a gas leak required detection of a small increase on a large background. Events such as passing near a source region of $CH_4$ (such as a farm), or an increase in the altitude of the airplane (an increase in the atmospheric path length) might result in the false signature of a leak.

To reduce the influence of the background, some past attempts have tried to detect the excess $CH_4$ of a natural gas leak by detecting the absorption of $CH_4$ in the long wavelength infrared region (for example, at 7.8 μm or 2180 cm$^{-1}$). This provides the advantage that the upwelling radiation is primarily emitted from the earth's surface. This minimises the background $CH_4$, as only the $CH_4$ located between the airplane and the earth's surface is detected.

However, for underground pipe since the temperature of the surface and the leaked $CH_4$ are nearly the same, the radiative contrast between the surface and the leaked methane is very small, greatly reducing the detectivity/detectability of the leak. Also, the thermal noise introduced within the instrument itself becomes a serious design constraint. Using a shorter wavelength absorption band of $CH_4$ could potentially help, as the upwelling radiation would be primarily from the sun. This would greatly increase the radiative contrast between the source and the "leaked" gas, and significantly reduce the thermal noise within the instrument. However, the background of $CH_4$ becomes very large, as the solar radiation reaching the instrument would have passed through entire atmosphere.

SUMMARY OF THE INVENTION

According to an aspect of the invention, leaks from natural gas are detected by remote detection of radiation that has passed through a concentration of ethane gas.

Ethane, $C_2H_6$, is a minor constituent in natural gas, comprising up to 20% of unprocessed natural gas, and approximately 2.5% of processed natural gas. It has the distinct advantage for detection over $CH_4$ in that it exists in the atmosphere in very minute quantities (global annual average concentration of 860 ppt). Therefore, the natural background is very small (2000 times smaller than $CH_4$).

The two main sources of $C_2H_6$ in the atmosphere are from leaked natural gas and biomass burning (both of roughly equivalent magnitudes). The main sink is by reaction with the hydroxyl (OH) radical. $C_2H_6$ has a strong absorption/emission band(s) at 3000 cm$^{-1}$ (3.33 μm). In this spectral region, the upwelling radiation will consist primarily of reflected solar radiation. Also, thermal noise within the instrument is significantly reduced at these shorter wavelengths. This combination of a tiny background, a strong spectral signature in a "solar" region of the spectrum, and reduced thermal noise makes $C_2H_6$ suitable for the detection of natural gas pipeline leaks. Preferably, the ethane is detected by using the ethane absorption/emission band(s) at 3000 cm$^{-1}$.

According to a further aspect of the invention, the ethane is detected by tuning the gas filter correlation radiometer to detect ethane using an ethane absorption peak at a bandwidth of 2850 to 3075 cm$^{-1}$.

According to a further aspect of the invention, the ethane is detected by tuning the gas filter correlation radiometer to detect ethane using an ethane absorption peak at a bandwidth up to 150 cm$^{-1}$ above or below 3000 cm$^{-1}$.

According to a further aspect of the invention, remote sensing of leaked gas, such as leaked ethane from natural gas pipelines, is carried out by using a gas filter correlation radiometer (GFCR). In a further aspect of the invention, the gas filter correlation radiometer comprises a window in a housing; optics defining a first optical path and a second optical path between the window and a detector section mounted in the housing; a beam splitter mounted in the housing as part of the optics for directing radiation entering the window from an outside source to divide the radiation between the first optical path and the second optical path; the first optical path having a first gas path length and the second optical path having a second gas path length, the first gas path length being different from the second gas path length; and electronics for processing signals produced by the detector section section as a result of radiation being directed by the optics onto the detector section. The gas path length is provided by gas filters containing differing amounts of the target gas, such as ethane, preferably with one of the optical paths having zero gas path length.

According to a further aspect of the invention, the beam splitter comprises a bi-prism.

According to a further aspect of the invention, the detector section further comprises a first detector on the first optical path and a second detector on the second optical path, and corresponding pixels on the first detector and second detector having collocated fields of view and being sampled synchronously.

According to a further aspect of the invention, the detector section detects radiation using a pushbroom imaging technique.

These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which.

DETAILED DESCRIPTION OF PREFERRED EMBODIMENTS

In this patent document, the word "comprising" is used in its non-limiting sense to mean that items following the word in the sentence are included and that items not specifically mentioned are not excluded. The use of the indefinite article "a" in the claims before an element means that one of the elements is specified, but does not specifically exclude others of the elements being present, unless the context clearly requires that there be one and only one of the elements.

The instrument used in this invention is a type of gas-filter correlation radiometer (GFCR). GFCRs have been used in different configurations for over 3 decades in remote sensing instrumentation.

Figure 1:
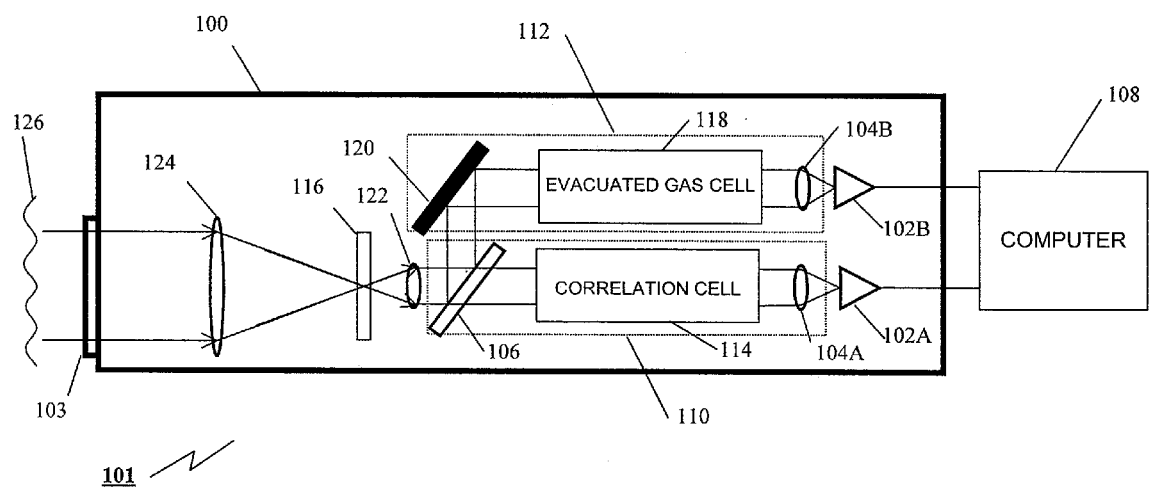
FIG. 1 is a schematic of the gas filter correlation radiometer.
Figure 2:
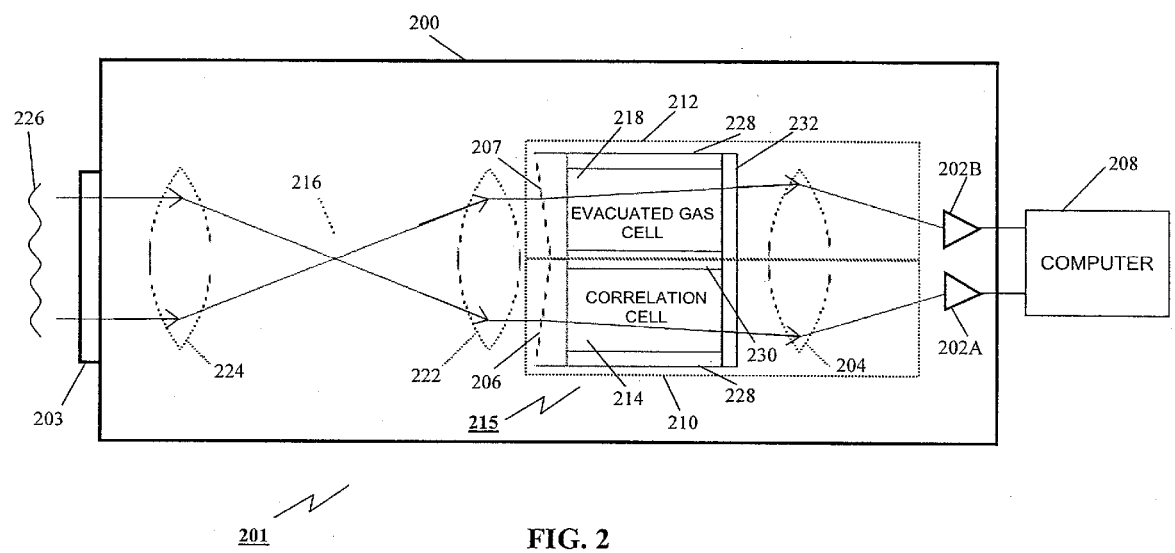
FIG. 2 is a schematic of an alternative embodiment of the gas filter correlation radiometer.

Referring to FIG. 1, there is shown a GFCR 101 incorporated within a housing 100, with a detector section, such as a pair of photodiode arrays 102A, 102B mounted in the housing. Radiation from source 126 passes through a window 103 in the housing 100, is collected by collector optic 124 and filtered by bandpass filter 116 and then directed by collimating lens 122 onto beam splitter 106. In an exemplary embodiment, a 40 cm$^{-1}$ wide band-pass filter 116 centred at 2988 cm$^{-1}$ is specified. The filter width is 1.3% of the central wavenumber. The passband of filter 116 is selected to include the ethane absorption peak at 3000 cm$^{-1}$ and exclude radiation falling outside of the peak. Beam splitter 106 formed by a partially reflective mirror splits the radiation from the radiation source 126 along paths 110 and 112. On the first radiation path 110, the radiation passes through gas correlation cell 114 and is focused by detector lens 104A onto the photodiode 102A. On the second radiation path 112, the radiation is directed by mirror 120 through an evacuated gas cell 118 and is focused by lens 104B onto photodiode 102B. The gas correlation cell 114, also called a gas filter or absorption cell, contains a gas, such as ethane, to be detected. The gas correlation cell 114 may for example be a 1 cm cell with for example a concentration of ethane provided by one atmosphere of pure $C_2H_6$. The second path 112 has a different path length of $C_2H_6$, such as may be obtained by providing the cell 118 with for example no $C_2H_6$, as for example an evacuated gas cell or a cell containing a gas that is optically neutral in relation to the ethane spectra of interest. The output of the photodiodes 102A, 102B is provided to suitable electronics, such as a computer 108, for processing. The GFCR 101 may use a beam splitter, for example, in the form of a partially reflective mirror as shown in FIG. 1, or in the form of a bi-prism, as shown in FIG. 2, or may selectively direct the incoming radiation through separate paths, in a time division manner, using for example a chopper. The use of a beam splitter versus a chopper is a trade-off between simultaneity of the two received signals and loss of signal intensity. A beam splitter, such as a partially reflective mirror or a bi-prism, is preferred for gas leak detection because it provides simultaneous measurement of both detector signals. This can be important because the signals are fast varying due to the forward motion of the helicopter and the variation in the reflective surface.

A different optical configuration is shown in an alternative embodiment in FIG. 2. Radiation from source 226 passes through a window 203 in housing 200, is collected on collector optic 224 and focused to a field stop 216. The field stop 216 is used to limit the field of view. The radiation from source 226 is then directed by collimating lens 222 onto prisms 206 and 207 which form the front of a compound gas cell 215 formed by gas cell walls 228, gas cell separator 230, and a plane parallel gas cell window 232. The prisms 206 and 207 split the radiation from the radiation source 226 along paths 210 and 212 by causing the radiation to diverge while passing through gas cells 214 and 218. On the first radiation path 210, the radiation is directed by prism 206 through gas correlation cell 214 and is focused by detector lens 204 onto the photodiode 202A. On the second radiation path 212, the radiation is directed by the prism 207 through an evacuated gas cell 218 and is focused by detector lens 204 onto photodiode 202B.

The compound gas cell 215 with prisms 206 and 207 may also be located between the field stop 216 and the collimating lens 222, or between the detector lens 204 and the photodiodes 202A and 202B. Likewise, the prisms 206 and 207 may be located at either the front of the compound gas cell 215 or at the back of the compound gas cell 215.

The gas correlation cell 214, also called a gas filter or absorption cell, contains a gas, such as ethane, to be detected. The gas correlation cell 214 may for example be a 1 cm cell with for example a concentration of ethane provided by one atmosphere of pure C2H6. The second path 212 has a different path length of C2H6, such as may be obtained by providing the cell 218 with for example no C2H6, as for example an evacuated gas cell or a cell containing a gas that is optically neutral in relation to the ethane spectra of interest. The output of the photodiodes 202A, 202B is provided to suitable electronics, such as computer 208, for processing.

The detector signal on the path 112 is:

$$S_1 = G \int_{\lambda_1}^{\lambda_2} I_\lambda \tau_{filter} \, d\lambda$$

where $I_\lambda$ is the intensity of the radiation from the radiation source 126, $\tau_{filter}$ is the transmissivity of the filter 116, $\lambda_1$ is the low pass of the filter 116, $\lambda_2$ is the high pass of the filter 116 and G is the gain of the photodiode 102B.

The detector signal on the path 110 is:

$$S_2 = G \int_{\lambda_1}^{\lambda_2} I_\lambda \tau_{filter} \tau_{corr.cell} \, d\lambda$$

where $\tau_{corr\ cell}$ is the transmissivity of the correlation cell 114.

If $$S_{avg} = \frac{S_1 + S_2}{2}$$

and $S_{diff}=S_1-S_2$, then the calculation made by the computer is:

$$S_{inst} = \frac{S_{diff}}{S_{avg}},$$

which yields a signal that is dependent on the presence of the target gas in the radiation path from the source 126 to the photodetector 102B. The calculation of the difference in the received signals for both optical paths is made for each pixel of the photodetectors 102A, 102B to yield an image of the field of view that may be displayed on a monitor.

Figure 3:
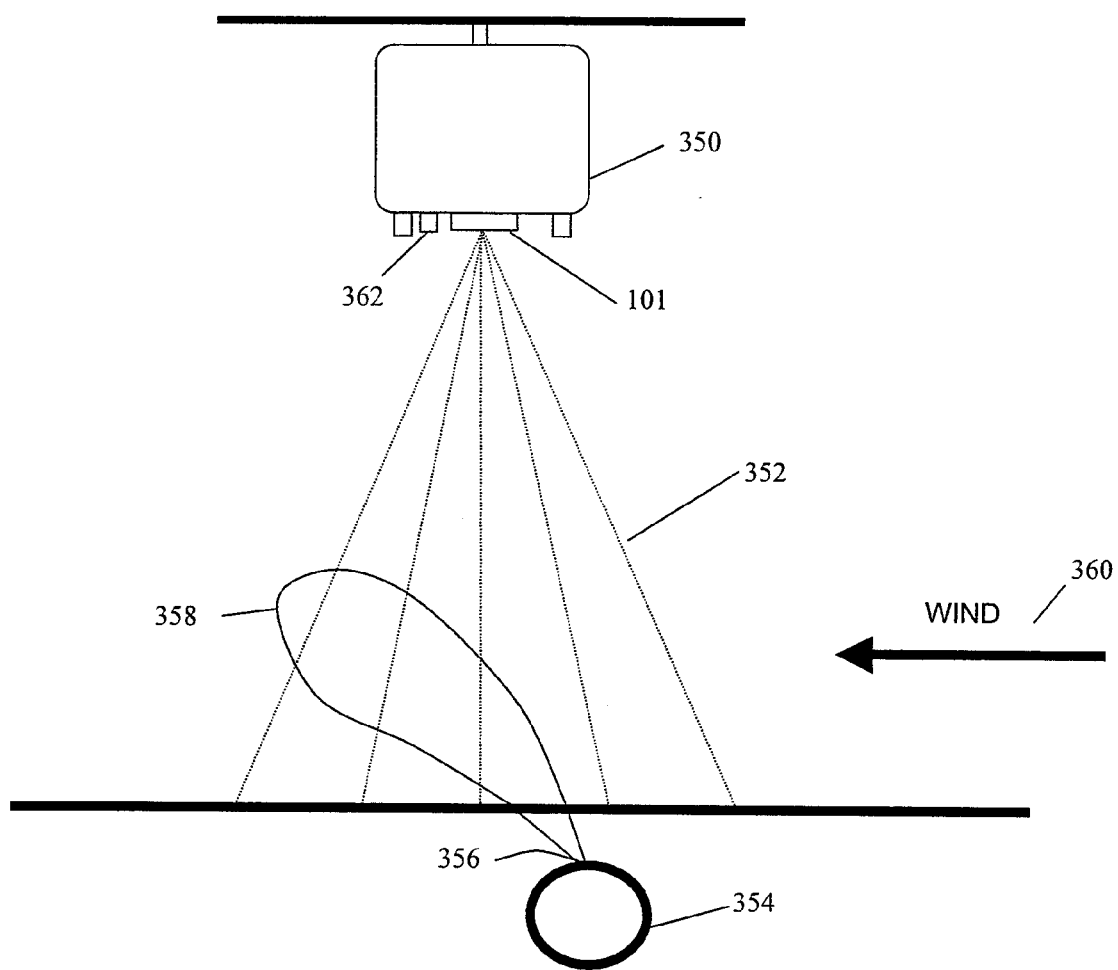
FIG. 3 depicts a helicopter using the gas filter correlation radiometer to detect a leak in a pipeline.
Figure 5:
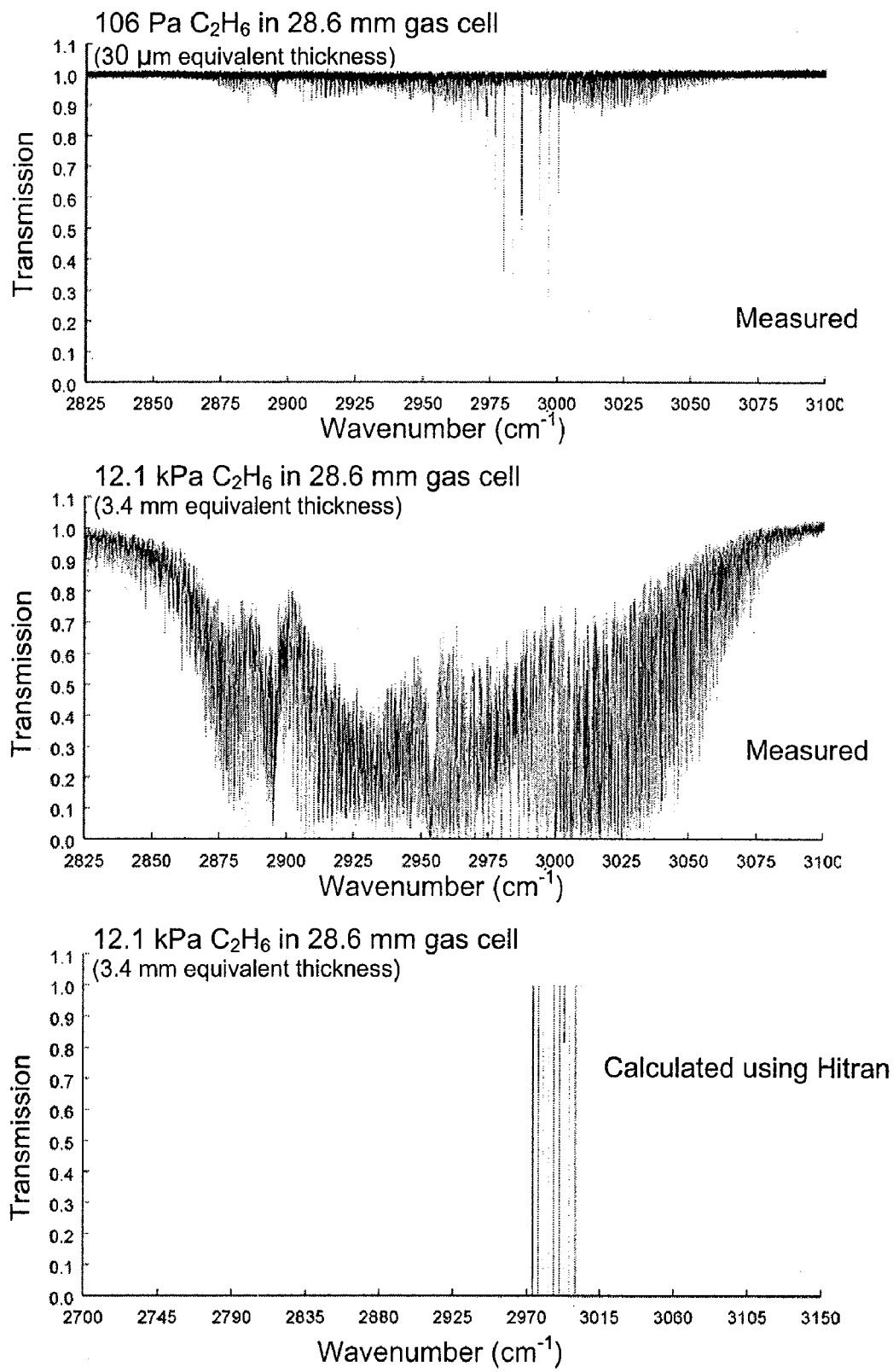
FIG. 5 shows, upper graph, a spectra of $C_2H_6$ in a 28.6 mm gas cell with 106 Pa of pure $C_2H_6$, middle graph, a high resolution spectra of $C_2H_6$ in a 28.6 mm gas cell with 12.1 kPa of pure $C_2H_6$ and, lower graph, a calculation of the spectra using the Hitran line database.

FIG. 3 shows the manner of use of the GFCR 101 shown in FIG. 1. A helicopter 350 traverses a pipeline 354 with a GFCR 101 having a field of view 352 oriented towards the pipeline 354. The GFCR 101 is tuned to detect ethane by appropriate selection of the bandpass of the filter 116, and the gas filter 114 contains a sample of ethane. If a leak 356 exists in the pipeline 354, the presence of ethane in the resulting plume 358 that may be moved by the presence of wind 360 will be detected using the GFCR 101. The presence of a leak is indicated by for example displaying the received signal using a monitor that is provided as part of the computer 108. Pixels on the monitor display corresponding to detected ethane may be coloured to enhance the image. Other methods of indication of the presence of a leak may be used such as detecting a concentration of ethane in the path between helicopter 350 and the ground that exceeds a predetermined threshold, and providing an alarm. The threshold is determined readily by calibration of the radiometer and experimentation. FIG. 5 shows that the absorption spectra of ethane at $3000^{-1}$ cm is larger than the calculated spectrum from the Hitran database, with the result that ethane is unexpectedly a suitable candidate for the detection of pipeline gas leaks. Due to the remote sensing capabilities of the device, the GFCR does not have to fly through the plume in order to detect leaks. The GFCR measures the integrated column concentration of natural gas between the helicopter and the ground, regardless of where in this column the natural gas occurs.

Figure 4:
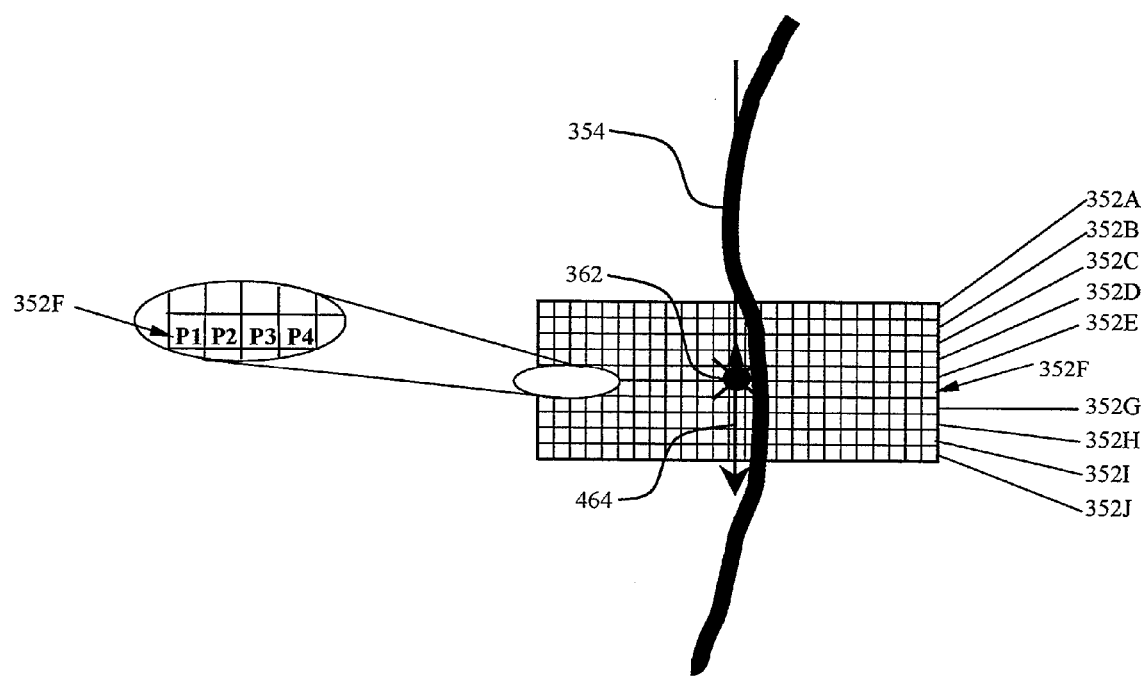
FIG. 4 depicts an overhead view of a helicopter traversing a pipeline and shows successive fields of view, including an exploded view of a portion of a field of view being sampled.

In one embodiment as shown in FIG. 4, the field of view 352 covers an area of 128 m², representing a swath 64 m long by 2 m wide. The long but narrow swath of the field of view 352 leads to an overall view of the pipeline 354 or target area through the use of a technique known as pushbroom imaging. As the helicopter 350 advances along the helicopter path 464 over the pipeline 354 or other target area, successive swaths below the helicopter 350 and perpendicular to the helicopter path 464 are detected by the GFCR 101. At a first time interval, the detectors 102A and 102B would sample signals from the field of view 352A, followed moments later by 352B, followed again by 352C and so on.

In FIG. 4, the field of view 352F represents the current swath of the target area being detected by the detectors 102A and 102B. Detectors 102A and 102B have corresponding pixels having collocated fields of view 352F where each 2 m×2 m cell of the field of view 352F is sampled synchronously by detectors 102A and 102B. Therefore, the cell marked P1 would be detected by a first pixel representing a portion of the field of view collocated and synchronized on detectors 102A and 102B. The cell marked P2 would be detected by a second pixel collocated and synchronized on detectors 102A and 102B. The same can be said for the cells marked P3 and P4 and so on. All cells P1 to P32 along a line would be detected simultaneously.

In an exemplary embodiment, the GFCR 101 operates using ambient background radiation that passes through the plume 358 of natural gas. The upwelling radiation field is comprised of reflected solar radiation, radiation emitted from the surface, plus upwelling emission from the atmosphere. For operation during cloudy periods or at night, a source of illumination 362 may be used. For example, a powerful 1600 W Tungsten Halogen bulb may be mounted on the helicopter 350, with an IR transmitting window (not shown) and a focusing mirror (not shown). This mirror focuses the emission from the illumination source 362 to a 5 m spot on the ground. Assuming a lambertian reflective surface and a reflectivity of 5%, the reflected intensity at the surface would be 0.048 W m⁻². This is roughly equivalent to (or slight greater than) the reflected intensity of sunlight. The illumination source 362 should be mounted to reduce vibrations that could increase the signal to noise ratio of the detected signal. In an alternative embodiment, the GFCR 101 may be mounted on a different type of vehicle, such as a truck, and driving the vehicle along a pipeline or other possible source of a gas leak. The GFCR 101 may also be tuned to detect other gases by selection of the bandpass of the filter 116.

The detected instrument signal is a function of the height of the natural gas column. For an atmospheric background concentration of 1 ppb of $C_2H_6$, the equivalent total atmospheric column thickness is approximately 8.5 μm. The equivalent $CH_4$ column thickness would be approximately 1700 times thicker.

A linear regression of the signal sensitivity between 0 and 4 mm of natural gas shows that the change in signal per mm of natural gas is $-1.69 \times 10^{-3}$ mm⁻¹. The measurement is actually detecting $C_2H_6$ which is assumed to be 2.5% of natural gas. Therefore, the detected columns of pure $C_2H_6$ are 40 times shorter than that of methane. Maximum sensitivity to $C_2H_6$ occurs at the lowest concentrations. This is the most desirable for detecting the smallest leaks.

Uncertainties may be introduced into the measurement by spectral interferences by other gases in the atmosphere (principally $H_2O$ and $CH_4$), variations in the surface emissivity, temperature variations in the atmospheric temperature, and variations in the altitude of the airplane. These uncertainties tend to reduce the sensitivity of the measurement to concentrations of natural gas, and variations may result in false signatures of leaks. The combined uncertainty is about +/−19 μm. This level of accuracy places a minimum limitation on the measurement's accuracy. Given a measurement resolution of $-1.69 \times 10^{-3}$ per mm natural gas, to measure a column height of ±19 μm a measurement precision of $\pm 3.2 \times 10^{-5}$ (i.e. a signal-to-noise ratio of 31,000) is required. Such a measurement precision may be obtained from the GFCR 101, and may be adjusted by for example varying the length of the absorption cell 114.

The sensitivity of the instrument is ultimately a function of the amount of energy that is collected and focussed onto the detector element. This in turn is a function of the field-of-view (FOV) of the instrument (which determines the surface resolution), the size of the collector optic 124, the size of the detector pixel in the photodiodes 102A, 102B, the transmission of the instrument, and the observation period (frequency) of the instrument. The FOV and the collector optic size directly affect the energy collected, as the larger the optic and FOV, the more photons collected. However, they also directly affect the detector pixel size, due to the principle of etendue ($A^{\Omega}$) conservation in an optical chain. The transmission of the instrument directly affects the energy collected as any losses in the system directly reduces the number of photons incident on the detector. And finally, the pixel size and observation period directly affect the noise-equivalent power (NEP) of the detector. In an exemplary embodiment, the aircraft may operate at a height of 30 m, with surface resolution 1.5 m, FOV solid angle $2.0 \times 10^{-3}$ sr, FOV 2.86°, collector optic diameter 12.2 cm, $A^\Omega$ product $2.29 \times 10^{-5}$ $m^2$ sr, transmission 75%, temperature 293K, observation time 10 ms (100 hz), detector element diameter 2 mm, detector FOV 170° and detector $D^*10^{11}$ cm $Hz^{0.5}$.

The upwelling radiance reaching the aircraft is calculated to be 0.04 W $m^{-2}$ $sr^{-1}$. This includes the energy lost due to absorption by atmospheric $H_2O$ and $CH_4$, and which is reduced to 0.03 W m-2 $sr^{-1}$. Assuming the instrument has a 12.2 cm diameter optic to collect upwelling radiation with a field-of-view of 2.86° and an instrument transmission of 75%, the collected energy by the instrument will be $5.2 \times 10^{-7}$ W. The noise equivalent power (NEP) for a 2 mm diameter liquid nitrogen cooled InSb detector would be $2 \times 10^{-11}$ W, providing a radiative S/N ratio of approximately 25,800. Given this level of precision and the calculated sensitivity to natural gas of $-1.69 \times 10^{-3}$ $mm^{-1}$, the measurement is able to detect below a 23 μm column of natural gas.

A person skilled in the art could make immaterial modifications to the invention described in this patent document without departing from the invention.

The embodiments of the invention in which an exclusive property or privileges is claimed are defined as follows:

1. A gas filter correlation radiometer, comprising:
    a window in a housing;
    optics defining a first optical path and a second optical path between the window and a detector section mounted in the housing;
    a bi-prism beam splitter comprising a pair of side-by-side prisms mounted transversely in the housing in relation to the first optical path and the second optical path as part of the optics for directing radiation entering the window from an outside source along two divergent paths offset from each other by refraction through the bi-prism beam splitter to divide the radiation between the first optical path and the second optical path;
    the first optical path having a first gas path length and the second optical path having a second gas path length, the first gas path length being different from the second gas path length; and
    electronics for processing signals produced by the detector section as a result of radiation being directed by the optics onto the detector section.

2. The gas filter correlation radiometer of claim 1 in which the gas filter correlation radiometer is tuned to detect ethane using the ethane absorption peak at 3000 $cm^{-1}$.

3. The gas filter correlation radiometer of claim 1 in which the gas filter correlation radiometer is tuned to detect ethane using an ethane absorption peak at a bandwidth of 2850 to 3075 $cm^{-1}$.

4. The gas filter correlation radiometer of claim 3 in which the gas filter correlation radiometer is tuned to detect ethane using an ethane absorption peak at a bandwidth up to 150 $cm^{-1}$ above or below 3000 $cm^{-1}$.

5. The gas filter correlation radiometer of claim 3 in which the gas filter correlation radiometer is tuned to detect ethane using the ethane absorption peak at 2850 to 3075 $cm^{-1}$ by incorporating a filter in the optics that selects radiation in a passband that includes the ethane absorption peak at 2850 to 3075 $cm^{-1}$.

6. The gas filter correlation radiometer of claim 1 in which the first optical path incorporates a gas filter containing ethane.

7. The gas filter correlation radiometer of claim 6 in which the second gas path length is lower than the first gas path length.

8. The gas filter correlation radiometer of claim 1 in which each prism of the side-by-side prisms has a thinner side and a thicker side, the pair of side-by-side prisms being joined along the respective thinner sides.

9. The gas filter correlation radiometer of claim 1 further comprising a source of illumination mounted with the gas filter correlation radiometer on board an aircraft.

10. The gas filter correlation radiometer of claim 3 further comprising a source of illumination mounted with the gas filter correlation radiometer on board an aircraft.

* * * * *